United States Patent [19]
Viera

[11] Patent Number: 5,464,023
[45] Date of Patent: Nov. 7, 1995

[54] MAGNETIC EXCHANGE DEVICE FOR CATHETERS

[75] Inventor: Fernando M. Viera, Hialeah, Fla.

[73] Assignee: Cordis Corporation, Miami Lakes, Fla.

[21] Appl. No.: 189,453

[22] Filed: Jan. 31, 1994

[51] Int. Cl.$^6$ ................................................. A61M 29/00
[52] U.S. Cl. ................................. 128/772; 128/657
[58] Field of Search .................... 128/772, 657; 604/93, 95, 164, 166, 170, 280, 282

[56] References Cited

U.S. PATENT DOCUMENTS

| | | |
|---|---|---|
| 3,674,014 | 7/1972 | Tillander . |
| 4,063,561 | 12/1977 | McKenna . |
| 4,244,362 | 1/1981 | Anderson ........................ 128/772 X |
| 4,593,687 | 6/1986 | Gray et al. . |
| 4,671,287 | 6/1987 | Fiddian-Green . |
| 4,922,923 | 5/1990 | Gambale et al. .................. 128/772 |
| 4,966,163 | 10/1990 | Kraus et al. ..................... 128/772 |
| 5,113,872 | 5/1992 | Jahrmarkt et al. ................ 128/772 |
| 5,117,838 | 6/1992 | Palmer et al. . |
| 5,133,364 | 7/1992 | Palermo et al. .................. 128/772 |
| 5,269,759 | 12/1993 | Hernandez et al. ............... 128/772 X |

OTHER PUBLICATIONS

Scimed Brochure entitled "The Magnetic Exchange Device Instructions For Use", 1993.

Primary Examiner—Sam Rimell
Attorney, Agent, or Firm—Gerstman, Ellis & McMillin, Ltd.

[57] ABSTRACT

Apparatus for facilitating the exchange of a catheter in the vascular system of a patient without displacing a guidewire which occupies the lumen of the catheter. The apparatus comprises a ferromagnetic rod which preferably defines a plurality of spaced, integral rings of ferromagnetic material distributed along the rod in substantially perpendicular relation to the axis thereof. The rod may be non-magnetized, or it may contain permanent magnets if desired. A connector may be provided for attaching the magnetic apparatus to a guidewire proximal end, or the device may be permanently attached to a guidewire end. A magnetic retainer which provides a magnetic field may be used to hold the ferromagnetic rod and the guidewire in a desired position as the catheter is either advanced or withdrawn while enclosing the ferromagnetic rod, so that the guidewire is retained while neither the guidewire nor the rod can be physically grasped.

19 Claims, 1 Drawing Sheet

5,464,023

MAGNETIC EXCHANGE DEVICE FOR CATHETERS

BACKGROUND OF THE INVENTION

In Hernandez, et al. U.S. Pat. No. 5,269,759 an apparatus and method are disclosed for facilitating balloon catheter exchange in the vascular system of a patient. The balloon catheter is advanced along a guidewire through the artery of a patient. Then, if there is a need to remove the catheter without displacing the position of the guidewire, a first magnetic element (such as ferromagnetic material, permanent magnetic material, or any other material that is capable of attracting or being attracted by a magnet) on the guidewire is retained by a second magnetic element which is located proximate to the balloon catheter and not fixed thereto. Thus, the balloon catheter may be withdrawn, enclosing the end of the guidewire in its lumen, while the guidewire is retained by the magnetic force exerted between the first magnetic element carried on the guidewire and the second magnetic element, which is typically located outside of the balloon catheter.

Also, Scimed Life Systems, Inc. of Maple Grove, Minn. has offered to the market a device under the name "The Magnet" in which a series of magnets in a housing surround a special guidewire, which is also manufactured by the same company, to fix the position of the guidewire by magnetic force as a catheter is withdrawn.

However, there is a need to provide a magnetic retention member for guidewires which provides a stronger magnetic field, to reduce the risk that a catheter being advanced or withdrawn breaks the magnetic bond which retains the guidewire, causing it to advance or retract with the catheter.

Also, conventional guidewires require a proximally mounted magnetic unit, to be effectively retained by a magnetic retainer as their proximal ends are surrounded by a moving catheter.

By this invention, a magnetic exchange device is provided which may be attached to guidewires which are of conventional design, and which have no significant magnetic retention capability, since, typically, guidewires are made of a nonmagnetic stainless steel. Thus, by this invention, if it becomes necessary to remove a conventional catheter overlying a guidewire in a patient's arterial system without removal of the guidewire, this can be accomplished by this invention even with a conventional, nonmagnetic guidewire without the use of a very long and inconvenient guidewire extension such as the extension disclosed in Gambale et al. U.S. Pat. No. 4,917,103.

DESCRIPTION OF THE INVENTION

By this invention, an apparatus is provided for facilitating the exchange of a catheter in the vascular system of a patient without displacing a guidewire, which guidewire has a distal and a proximal end, and in which the guidewire occupies a lumen of the catheter. The apparatus comprises magnetic attraction means which are proportioned to fit into the catheter lumen. A connector may also be provided for attaching the magnetic attraction means to the guidewire proximal end, this connector being also proportioned to fit into the catheter lumen. The apparatus preferably has a maximum diameter of 0.01 to 0.03 inch.

Preferably, the magnetic attraction means comprises a ferromagnetic rod which defines a plurality of spaced, integral rings of ferromagnetic material distributed along the rod in substantially perpendicular relation to the axis of the rod. Typically about 30 to 60 of the spaced integral rings may be present, with the rings being preferably of a diameter of about 0.01–0.02 inch, and being of a width and a spacing so that the ferromagnetic rod may typically be about 3 to 8 inches long. Preferably, the ferromagnetic rod and integral rings are made from a single metal piece.

If the particular alloy of the ferromagnetic rod is sensitive to corrosion, or for any other desired reason, the rod may be enclosed in a tube of non-ferromagnetic material, either metal or plastic.

Preferably, the diameter of the ferromagnetic rod sections between the spaced, integral rings is as small as practicable, since, generally, a reduction in diameter of the rod between the spaced, integral rings tends to increase the strength of the magnetic retention of the ferromagnetic rod. Preferably, the diameter of the ferromagnetic rod between the rings may be on the order of 0.003 to 0.008 inch, and of less diameter than the rings that they carry, which may preferably have a diameter of about 0.01 to 0.02 inch and a thickness of about 0.005 to 0.008 inch.

The rings are preferably spaced from each other by about 0.05 to 0.2 inch.

Thus, the connector-carrying apparatus of this invention may be attached to a guidewire which extends into the vascular system of a patient. The apparatus and guidewire may be surrounded by an intravascular catheter, with at least the magnetic attraction means of the apparatus and the adjacent, surrounding portion of the catheter being surrounded by a magnetic retainer which may comprise a series of strong magnets, or an electromagnet, in a manner which is generally known and described for example in the above cited Hernandez, et al. patent. The magnetic retainer thus holds by magnetic force the magnetic attraction means in a stationary position, permitting the catheter to be moved along the guidewire without displacement of the guidewire.

The connector of this invention may be any desired connector which is suitable and appropriate for retention of a guidewire as contemplated above. Specifically, the connector may be in accordance with the disclosures of U.S. Pat. Nos. 5,113,872 or 5,117,838, the disclosures of which are incorporated herein by reference. Such a connector may comprise a coiled spring carried by the apparatus of this invention. The coiled spring is proportioned and constructed to receive and grippingly engage and lock against a proximal end of a guidewire. A tube is received over the coiled spring and is carried by the apparatus of this invention. A retention member is provided for maintaining the spring in the tube.

Thus, one can attach the connector of an apparatus of this invention which carries magnetic attraction means to the end of a guidewire which extends into the vascular system of a patient. One can then withdraw an intravascular catheter about the guidewire and the apparatus, while retaining by magnetic force the magnetic attraction means in a stationary position as the catheter is moved along the guidewire and the apparatus, to effect an exchange of an intravascular catheter about a guidewire without displacing the guidewire, and without the need of a guidewire extension. This can be accomplished with conventional catheters which are not of a rapid exchange design, and which are thus free of side slots and apertures.

DESCRIPTION OF SPECIFIC EMBODIMENTS

Figure 1:
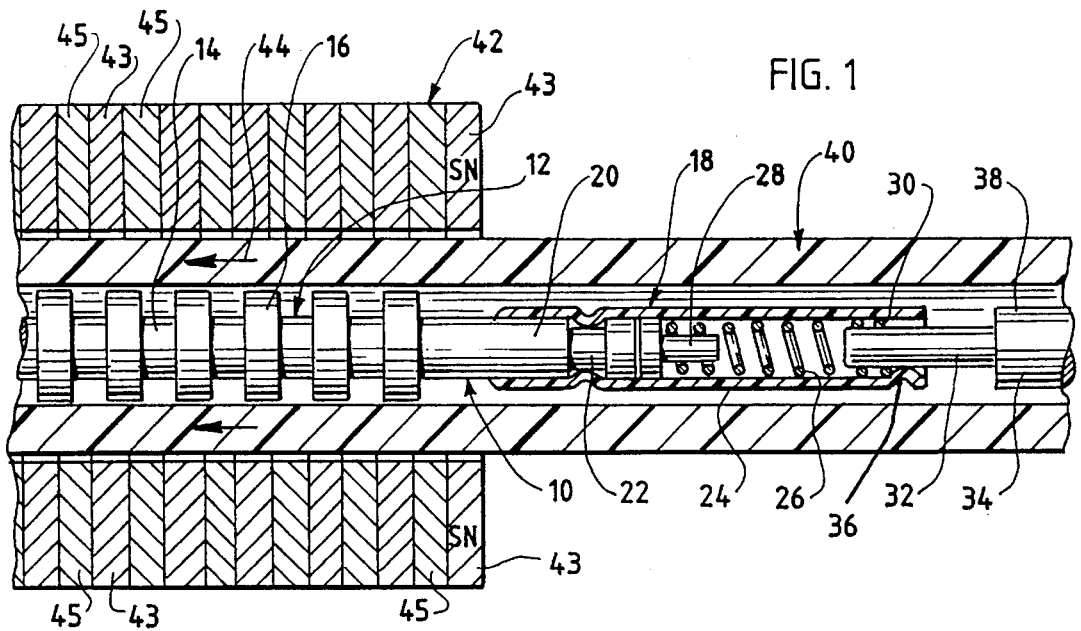
FIG. 1 is an enlarged view, taken in section, of the apparatus of this invention for facilitating the exchange of a catheter about a guidewire without displacing the guidewire.

Referring to the drawings, the magnetic exchange apparatus 10 of this invention is shown in a highly enlarged view, taken in longitudinal section. Exchange apparatus 10 is shown to have a magnetic attraction member 12 which is preferably made of a single, integral rod of ferromagnetic material which defines rod sections 14 between a plurality of spaced, integral rings 16. For example, the ferromagnetic material may be any appropriate ferromagnetic iron alloy, for example vanadium Permendur alloy made by the Hyperco Company, or chrome 8 alloy (410 stainless steel), which is a ferromagnetic form of stainless steel. Rod 12 may carry permanent magnets, or it may be an integral piece of unmagnetized, ferromagnetic material, for example.

Specifically, ferromagnetic rod 12 may be about six inches in length, carrying about fifty of the spaced, integral rings 16. For example, rings 16 may be about 0.01 inch in diameter and 0.065 inch thick. The length of each section 14 of rod 12 between the respective rings 16 may be about 0.075 inch. The diameter of each segment 4 of rod 12 spaced between the rings may be about 0.003 to 0.006 inch, with smaller diameters of rod sections 14 increasing the magnetic retention effect capable with a magnetic attraction member 12 of this design.

Magnetic attraction member 12 may be integrally attached at one end thereof to a connector 18, which may generally be of the function and structure as described in U.S. Pat. Nos. 5,113,872 or 5,117,838. Connector 18 defines a connector base 20, which may be an integral part of rod 12, defining an annular recess 22 for retention of metal sleeve 24 by crimping as shown.

Coiled spring 26 is carried within sleeve 24, having a first end which is secured on a pin 28 and a free second end 30 which is proportioned and arranged to receive and to grippingly engage and lock against a proximal end pin 32 of a guidewire 34, which may be of conventional design. Retention crimp 36 is provided in tube 24 to maintain spring 26 in the tube.

This particular connector 18 is of a design sold by the Cordis Corporation under the brand name CINCH. Its reliable and disconnectable guidewire securing capability is well known and useable herein to secure ferromagnetic rod 12 to the proximal end of a guidewire.

Basically, connector 18 may be connected to and disconnected from guidewire 34 by a simple twisting action.

It is to be understood that other connectors may be utilized, including but not limited to crimps, frictional attachments of various kinds, threaded connectors, male/female connectors, etc.

Accordingly, during an angioplasty procedure, for example, guidewire 34 is emplaced into the arterial system of the patient with only a proximal end portion 38 projecting out from the patient's body by a short distance. Guidewire 34 is surrounded by a PCTA balloon catheter 40, for example, which is guided in its advancement through the arterial system by the presence of guidewire 34.

In the circumstance that the physician deems it necessary to replace balloon catheter 40 with another balloon catheter (with a larger balloon, for example), conventionally the physician must attach a cumbersome, lengthy guidewire extension to the end of guidewire 34. This requires the assistance of a technician who does little but handle the guidewire extension, which may be 100 or more cm. long. Otherwise, as one attempts to remove catheter 40, guidewire 34 may be pulled with it, and the important, advanced position of the guidewire in the arterial system may be lost.

If catheter 40 is of the well known "rapid exchange" type, other removal techniques can take place, but the rapid exchange catheters have their own array of disadvantages.

Also, if catheter 40 is not of the rapid exchange type, only the cumbersome attachment of the guidewire extension can be conventionally used to exchange catheters. However, by this invention, in that circumstance, the apparatus 10 of this invention may be applied to a conventional guidewire 34 as shown in FIG. 1. Then, as also shown in FIG. 1, a magnetic retainer 42 is shown to carry a stack of permanent ring magnets 43, separated by ferromagnetic rings 45. Retainer 42 may be placed in surrounding relation around at least a portion of ferromagnetic rod 12 and outside of catheter 40, so that a strong magnetic field is exerted between rod 12 and magnetic retainer 42. This field is strengthened because of the specific design of the ferromagnetic rod 12 disclosed herein.

As catheter 40 is withdrawn in the direction shown by arrow 44, it can completely enclose rod 12 and move proximally without disrupting the magnetic retaining field exerted between rod 12 and magnetic retainer 42. Thus, neither the magnetic exchange device 10 nor the guidewire 34 are dislodged from their desired position as catheter 40 is withdrawn. Preferably, rod 12 may be longer than magnetic retainer 42, preferably at least one and one half times longer, so that rod 12 can occupy a plurality of magnetically retained positions within magnetic retainer 42. Specifically, rod 12 may be about 3 to 8 inches long.

Then, if desired, another catheter may be installed, being threaded around magnetic exchange device 10 and guidewire 34, and advanced into the patient's arterial system along the guidewire without distal displacement of either exchange device 10 or guidewire 34, even while ferromagnetic rod is completely enclosed in the advancing catheter, because of the magnetic retention force exerted between rod 12 and magnetic retainer 42.

Ferromagnetic rod 12 is preferably longer than magnetic retainer 42 so that guidewire 34 can be retained in the plurality of relative positions between rod 12 and retainer 42. In preferred designs, spaced rings 16 preferentially position themselves near magnets 43, which are preferably equally spaced to rings 16 to define a series of discrete positions of increased magnetic retention between rod 12 and retainer 42. Thus, any slippage of rod 12 between such positions can be felt by the user, to serve as a warning of such slippage.

Accordingly, a new method is provided for the exchange of catheters from around a conventional guidewire that, in its own right, may be nonmagnetic, as conventional guidewires are. Such a guidewire 34 is, for the first time, magnetically retained in its desired position by a releasably attached exchange device 12 in accordance with this invention.

Figure 3:
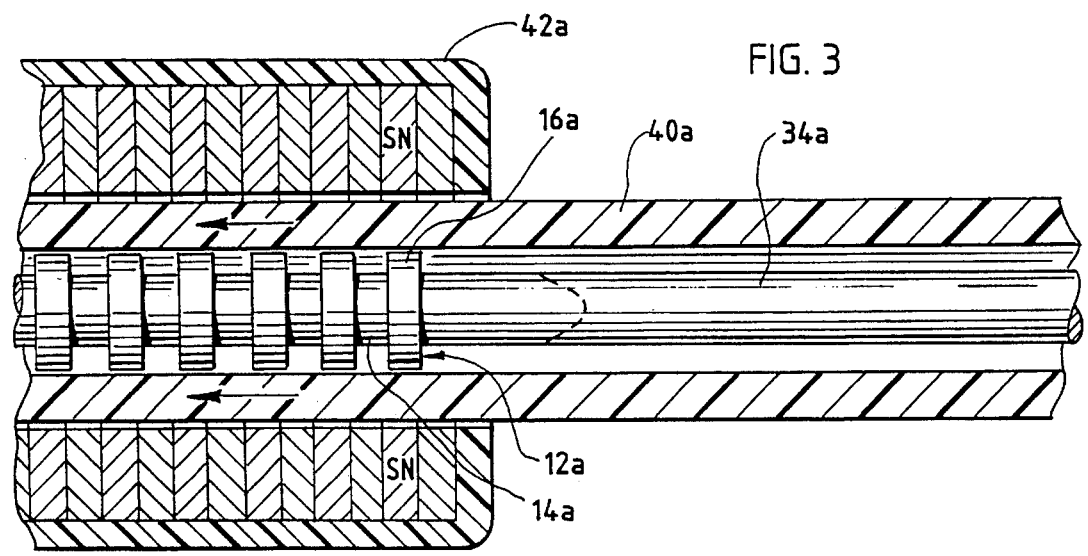
FIG. 3 is an enlarged, sectional view of the apparatus which comprises a specific embodiment of magnetic attraction means integrally connected to the distal end of a guidewire.

Referring to FIG. 3, a magnetic exchange device comprises a ferromagnetic rod 12a having spaced rings 16a and spacing rod segments 14a, together as a typically integral ferromagnetic piece. Ferromagnetic rod 12a in this embodiment is secured by welding, crimping, or the like to the proximal end of a guidewire 34a, which may be made of a nonmagnetic stainless steel or the like. Thus, such a guidewire 34a having ferromagnetic rod 12a permanently secured on its proximal end is as equally capable as the embodiment of FIG. 1 for being magnetically retained by retainer member 42a. Catheter 40a which encloses ferromagnetic rod 12a, is advanced or withdrawn therealong, and along guidewire 34a, without guidewire displacement.

Figure 2:
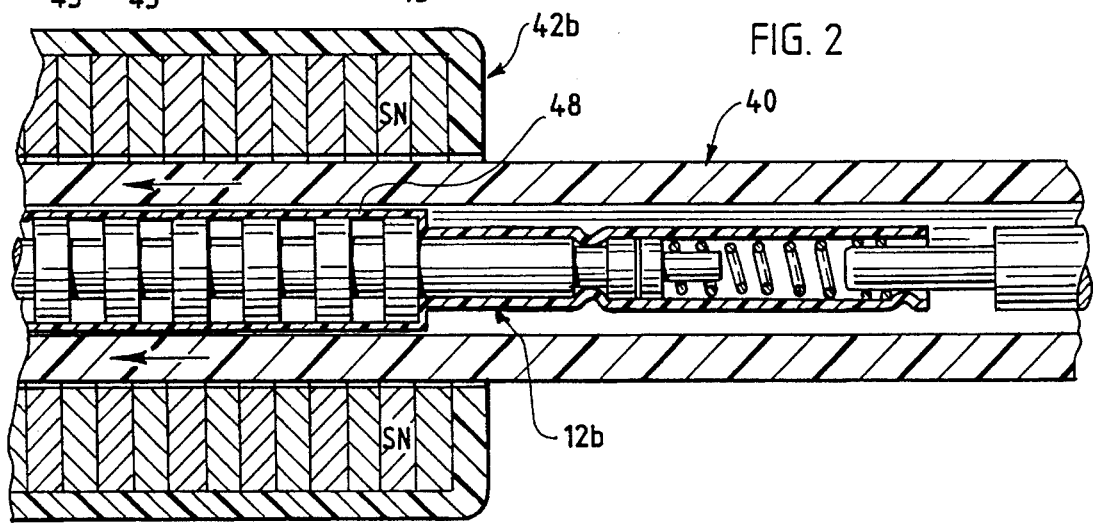
FIG. 2 is an enlarged, sectional view of apparatus similar to FIG. 1 in which the magnetic attraction member is enclosed in an outer sleeve made of non-magnetic material.

FIG. 2 is similar to the device of FIG. 1, but shows a ferromagnetic rod 12b which may be of a design similar to either FIG. 1 or FIG. 2, having a sleeve 48 which seals at least part of ferromagnetic rod 12b from the exterior for protection. This may be particularly desirable in the case where ferromagnetic rod 12b is made of a material that corrodes easily, or is toxic. Sleeve 48 may be made of a nonmagnetic, medically acceptable material which may either be metal or plastic, so that there is no interference between a magnetic field generated between rod 12b and a magnetic retainer 42b. This permits the present embodiment to perform in a manner which is substantially identical to either of the previously described embodiments. Specifically, sleeve 48 may be desired for use when magnetic rod 12b is made of vanadium Permendur alloy, or any other alloy which is subject to corrosion.

Thus, a magnetic exchange device is provided which may be integrally carried on a guidewire, or may be attached as desired to conventional guidewires as the need arises, to facilitate rapid and convenient exchange of catheters during surgical procedures such as PTCA, while avoiding the need for especially designed catheters capable of rapid exchange, and avoiding the need for guidewire extensions.

The above has been offered for illustrative purposes only, and is not intended to limit the scope of the invention of this application, which is as defined in the claims below.

That which is claimed is:

1. A guidewire and a magnetic retainer for facilitating the exchange of a catheter in the vascular system of a patient without displacing said guidewire, said guidewire having a distal end and a proximal end which occupies a lumen of said catheter, said guidewire carrying on its proximal end magnetic attraction means proportioned to fit into the catheter lumen, said magnetic attraction means comprising a ferromagnetic rod which defines a plurality of spaced, integral rings of ferromagnetic material distributed along said rod in substantially perpendicular relation to the axis of said rod; said magnetic retainer being positioned adjacent said ferromagnetic rod to hold said ferromagnetic rod and guidewire in a stationary position relative to said magnetic retainer by a magnetic force while permitting the catheter to slide along said guidewire, said magnetic retainer comprising a plurality of spaced magnets said plurality of magnets extending substantially parallel to said spaced, integral rings for magnetic retention thereof.

2. The guidewire and retainer of claim 1 and retainer in which said ferromagnetic rod and integral rings are made from a single ferromagnetic metal piece free of permanent magnets.

3. The guidewire and retainer of claim 1 which said magnetic attraction means has a maximum diameter of 0.01 to 0.03 inch.

4. The guidewire and retainer of claim 1 in which said ferromagnetic rod is enclosed in a pore-free tube of non-ferromagnetic material to seal said ferromagnetic rod from corrosion.

5. The guidewire and retainer of claim 1 in which from about 10 to 100 of said spaced, integral rings are present.

6. The guidewire and retainer of claim 1 in which said ferromagnetic rod is about 2 to 16 inches long.

7. The guidewire and retainer of claim 1 which extends into the vascular system of a patient, said rod and guidewire being surrounded by an intravascular catheter.

8. The guidewire and retainer of claim 1 in which said plurality of magnets are separated by ferromagnetic spacers.

9. The guidewire and retainer of claim 1 in which said plurality of magnets are essentially equally spaced corresponding to the spacing of said integral rings.

10. Apparatus for facilitating the exchange of a catheter in a vascular system of a patient without displacing a guidewire which occupies the lumen of said catheter, said guidewire having a distal end and a proximal end, said apparatus comprising:

magnetic attraction means attached to the proximal end of said guidewire, said magnetic attraction means being proportioned to fit into the catheter lumen, said magnetic attraction means comprising a ferromagnetic rod which defines a plurality of spaced, integral rings of ferromagnetic material distributed along said rod in substantially perpendicular relation to the axis of said rod, and a magnetic retainer which surrounds said ferromagnetic rod and holds the magnetic attraction means in a stationary position by magnetic force, said magnetic retainer comprising a plurality of spaced magnets, the spacing of said magnets substantially corresponding to the spacing of said integral rings.

11. The apparatus of claim 10 in which from about 10 to 100 of said spaced, integral rings are present.

12. The apparatus of claim 11 in which said ferromagnetic rod is about 3 to 8 inches long.

13. The apparatus of claim 8 in which said ferromagnetic rod and integral rings are made from a single ferromagnetic metal piece and are free of permanent magnets.

14. The apparatus of claim 10 in which said ferromagnetic rod is enclosed in a pore-free tube of non-ferromagnetic material to seal said ferromagnetic rod from corrosion.

15. The apparatus of claim 10 in which said guidewire extends into the vascular system of a patient, said apparatus and guidewire being surrounded by said intravascular catheter, the catheter being engaged by said magnetic retainer which holds the magnetic attraction means in a stationary position by magnetic force as the catheter is moved along said guidewire and said apparatus.

16. The apparatus of claim 15 in which said ferromagnetic rod is at least 1½ times the length of said magnetic retainer so that the guidewire can be retained in a plurality of relative positions of said magnetic attraction means and the magnetic retainer.

17. The method which comprises retaining a guidewire in a position within the cardiovascular system of a patient while withdrawing a catheter positioned around said guidewire from said cardiovascular system, including the steps of bringing a magnetic retainer member into proximity of magnetic attraction means secured to the proximal end of said guidewire, said magnetic attraction means comprising a ferromagnetic rod which defines a plurality of spaced, integral rings of ferromagnetic material distributed along said rod in substantially perpendicular relation to the axis of said rod; said magnetic retainer member comprising a plurality of magnets that are essentially equally spaced to the spacing of said spaced, integral rings and generally parallel thereto in a position to exert magnetic retention force between said retainer member and said ferromagnetic rod; and thereafter withdrawing said catheter from the patient between the magnetic retainer member and the magnetic attraction means without displacing the guidewire from a position within the patient.

18. The method of claim 17 in which said magnetic attraction means is longer than said magnetic retainer member so that the guidewire can be retained in a plurality of relative positions between said magnetic attraction means and magnetic retainer member, said retainer member defining magnets that are essentially equally spaced compared with said rings.

19. The method of claim 18 in which one thereafter advances a second catheter about said magnetic attraction means and guidewire along the guidewire into the vascular system of the patient.

* * * * *